(12) United States Patent
Chu et al.

(10) Patent No.: US 7,955,380 B2
(45) Date of Patent: Jun. 7, 2011

(54) PROSTHESIS FIXATION APPARATUS AND METHODS

(75) Inventors: Jack Chu, Santa Rosa, CA (US);
Jonathan Morris, Keller, TX (US);
James Machek, Santa Rosa, CA (US)

(73) Assignee: Medtronic Vascular, Inc., Santa Rosa, CA (US)

( * ) Notice: Subject to any disclaimer, the term of this patent is extended or adjusted under 35 U.S.C. 154(b) by 1441 days.

(21) Appl. No.: 11/276,877

(22) Filed: Mar. 17, 2006

(65) Prior Publication Data

US 2007/0219627 A1    Sep. 20, 2007

(51) Int. Cl.
*A61F 2/06* (2006.01)
(52) U.S. Cl. .............. 623/1.36; 623/1.11; 623/1.23
(58) Field of Classification Search ............ 623/1.11, 623/1.36, 1.23, 1.14, 1.12, 1.13; 606/219, 606/139, 143, 151; 227/175.1–182.1
See application file for complete search history.

(56) References Cited

U.S. PATENT DOCUMENTS

| | | | | |
|---|---|---|---|---|
| 816,026 A | * | 3/1906 | Meier | 606/221 |
| 3,716,058 A | * | 2/1973 | Tanner, Jr. | 606/221 |
| 4,485,816 A | | 12/1984 | Krumme | |
| 4,787,899 A | * | 11/1988 | Lazarus | 623/1.11 |
| 5,002,562 A | | 3/1991 | Oberlander | |
| 5,207,695 A | * | 5/1993 | Trout, III | 623/1.36 |
| 5,364,406 A | | 11/1994 | Sewell, Jr. | |
| 5,409,495 A | * | 4/1995 | Osborn | 623/1.11 |
| 5,601,572 A | | 2/1997 | Middleman et al. | |
| 5,713,907 A | | 2/1998 | Hogendijk et al. | |
| 5,713,948 A | * | 2/1998 | Uflacker | 623/1.23 |
| 5,800,526 A | * | 9/1998 | Anderson et al. | 623/1.16 |
| 5,843,169 A | | 12/1998 | Taheri | |
| 6,004,347 A | * | 12/1999 | McNamara et al. | 623/23.64 |
| 6,026,814 A | * | 2/2000 | LaFontaine et al. | 128/898 |
| 6,030,413 A | | 2/2000 | Lazarus | |
| 6,149,660 A | * | 11/2000 | Laufer et al. | 606/143 |
| 6,187,036 B1 | * | 2/2001 | Shaolian et al. | 623/1.15 |
| 6,210,435 B1 | * | 4/2001 | Piplani et al. | 623/1.35 |
| 6,221,102 B1 | * | 4/2001 | Baker et al. | 623/1.36 |
| 6,248,116 B1 | * | 6/2001 | Chevillon et al. | 606/139 |
| 6,287,335 B1 | * | 9/2001 | Drasler et al. | 623/1.28 |

(Continued)

FOREIGN PATENT DOCUMENTS

WO    WO01/76509    10/2001

(Continued)

*Primary Examiner* — Gary Jackson
*Assistant Examiner* — Erin Colello

(57) ABSTRACT

A method of securing a prosthesis placed at a desired site in a passageway of a human body comprises delivering a fastener having a proximal piercing end portion and a distal piercing end portion to a site where a prosthesis having a tubular wall has been placed in the passageway, which has a wall, advancing the proximal piercing end portion beyond the prosthesis, penetrating the proximal piercing end portion into the wall of the passageway without passing the proximal piercing end portion through the tubular wall of the prosthesis, and passing the distal piercing end portion through the tubular wall of the prosthesis and into the wall of the passageway. One surgical fastener delivery apparatus for delivering a surgical fastener to a target site comprises a support having a first end, a second end, and a longitudinal axis and being adapted for placement in a passageway in a human body. A surgical fastener having a first piercing end portion, a second piercing end portion and a central portion extending therebetween and having a longitudinal axis is releasably mounted to the support with the central portion longitudinal axis generally parallel to the support longitudinal axis.

39 Claims, 12 Drawing Sheets

U.S. PATENT DOCUMENTS

| | | |
|---|---|---|
| 6,346,112 B2 | 2/2002 | Adams |
| 6,416,522 B1* | 7/2002 | Strecker .................. 606/143 |
| 6,475,222 B1* | 11/2002 | Berg et al. ................ 606/108 |
| 6,517,573 B1* | 2/2003 | Pollock et al. ............. 623/1.15 |
| 6,592,593 B1* | 7/2003 | Parodi et al. .............. 606/108 |
| 6,626,899 B2* | 9/2003 | Houser et al. .............. 606/14 |
| 6,656,215 B1 | 12/2003 | Yanez et al. |
| 6,695,859 B1 | 2/2004 | Golden et al. |
| 6,800,081 B2* | 10/2004 | Parodi ...................... 606/139 |
| 6,814,751 B2* | 11/2004 | Rosengart ................. 623/1.23 |
| 6,918,926 B2* | 7/2005 | Letort ...................... 623/1.13 |
| 6,926,690 B2* | 8/2005 | Renati ...................... 604/8 |
| 6,932,838 B2* | 8/2005 | Schwartz et al. .......... 623/1.23 |
| 7,007,698 B2* | 3/2006 | Thornton ................. 128/898 |
| 7,066,953 B2* | 6/2006 | Rosengart ................. 623/1.23 |
| 7,211,095 B2* | 5/2007 | Bachinski et al. .......... 606/153 |
| 7,322,992 B2* | 1/2008 | Trout et al. ................ 606/138 |
| 7,351,258 B2* | 4/2008 | Ricotta et al. ............. 623/1.36 |
| 7,524,330 B2* | 4/2009 | Berreklouw .............. 623/1.36 |
| 7,556,646 B2* | 7/2009 | Yang et al. ................ 623/2.11 |
| 7,556,647 B2* | 7/2009 | Drews et al. .............. 623/2.11 |
| 2001/0037142 A1* | 11/2001 | Stelter et al. .............. 623/1.23 |
| 2001/0039435 A1* | 11/2001 | Roue et al. ................ 606/216 |
| 2002/0108621 A1* | 8/2002 | Berg et al. ................. 128/898 |
| 2002/0165561 A1 | 11/2002 | Ainsworth et al. |
| 2003/0065385 A1* | 4/2003 | Weadock ................... 623/1.23 |
| 2003/0074055 A1* | 4/2003 | Haverkost ................. 623/1.16 |
| 2003/0120263 A1* | 6/2003 | Ouriel et al. ............... 606/1 |
| 2003/0176911 A1* | 9/2003 | Iancea et al. .............. 623/1.13 |
| 2003/0236570 A1* | 12/2003 | Cook et al. ................ 623/1.36 |
| 2004/0050393 A1 | 3/2004 | Golden et al. |
| 2004/0068276 A1 | 4/2004 | Golden et al. |
| 2004/0093057 A1* | 5/2004 | Bolduc et al. ............. 623/1.11 |
| 2004/0093063 A1 | 5/2004 | Wright et al. |
| 2004/0138683 A1 | 7/2004 | Shelton et al. |
| 2004/0138705 A1 | 7/2004 | Heino et al. |
| 2004/0176663 A1* | 9/2004 | Edoga et al. .............. 600/139 |
| 2004/0236356 A1* | 11/2004 | Rioux et al. .............. 606/144 |
| 2004/0236419 A1 | 11/2004 | Milo |
| 2005/0004582 A1* | 1/2005 | Edoga et al. .............. 606/139 |
| 2005/0021132 A1* | 1/2005 | Bolduc et al. ............. 623/1.35 |
| 2005/0033398 A1* | 2/2005 | Seguin ...................... 623/1.11 |
| 2005/0070924 A1 | 3/2005 | Schaller et al. |
| 2005/0075659 A1 | 4/2005 | Realyvasquez et al. |
| 2005/0080454 A1* | 4/2005 | Drews et al. .............. 606/221 |
| 2005/0096722 A1* | 5/2005 | Lootz et al. ............... 623/1.11 |
| 2005/0107871 A1 | 5/2005 | Realyvasquez et al. |
| 2005/0131429 A1* | 6/2005 | Ho et al. ................... 606/143 |
| 2005/0154401 A1* | 7/2005 | Weldon et al. ............ 606/139 |
| 2005/0273155 A1* | 12/2005 | Bahler et al. .............. 623/1.13 |
| 2006/0020333 A1* | 1/2006 | Lashinski et al. .......... 623/2.11 |
| 2006/0142835 A1* | 6/2006 | Spiridigliozzi et al. ..... 623/1.11 |
| 2006/0161244 A1* | 7/2006 | Seguin ...................... 623/1.23 |
| 2006/0293759 A1* | 12/2006 | Berg et al. ................. 623/23.7 |
| 2007/0010875 A1* | 1/2007 | Trout et al. ................ 623/1.36 |
| 2007/0021829 A1* | 1/2007 | Bolduc ...................... 623/1.36 |
| 2007/0050012 A1* | 3/2007 | Densford ................... 623/1.23 |
| 2007/0050019 A1* | 3/2007 | Hyde ........................ 623/2.11 |
| 2009/0270966 A1* | 10/2009 | Douk et al. ................ 623/1.11 |

FOREIGN PATENT DOCUMENTS

| | | |
|---|---|---|
| WO | WO02/085254 | 10/2002 |
| WO | WO 2005099627 A1 * | 10/2005 |

* cited by examiner

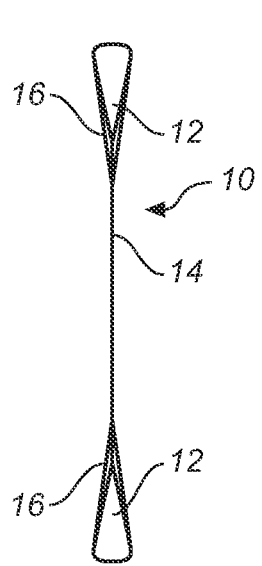
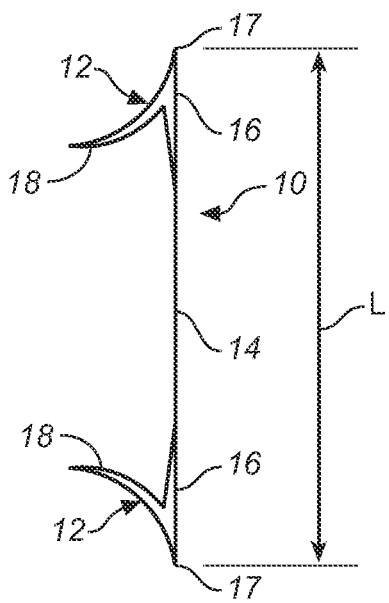
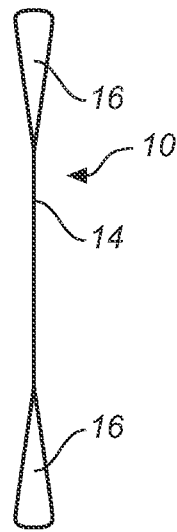
FIG. 1A  FIG. 1B  FIG. 1C
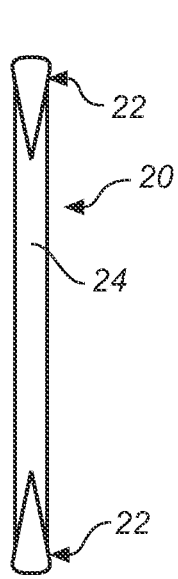
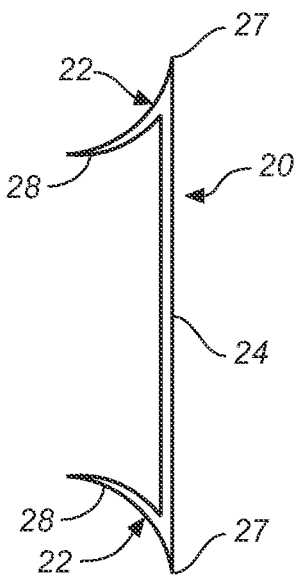
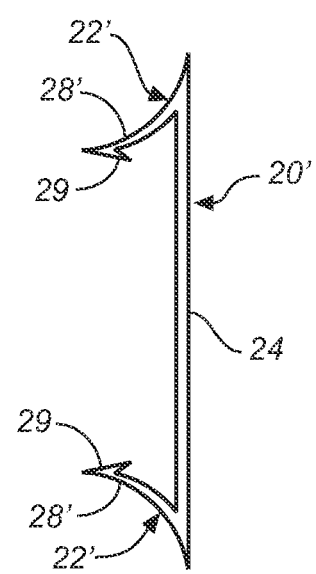
FIG. 2A  FIG. 2B  FIG. 2C

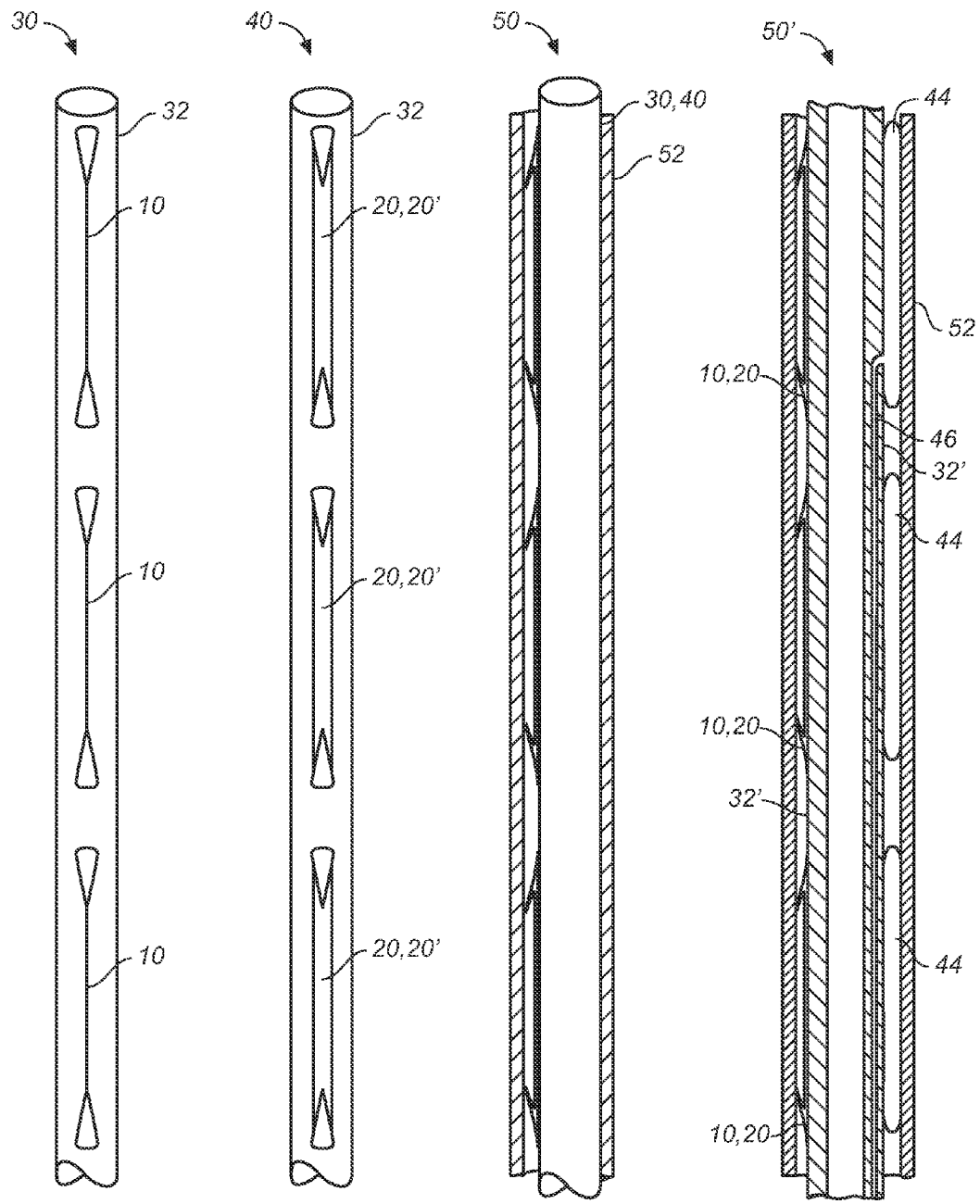

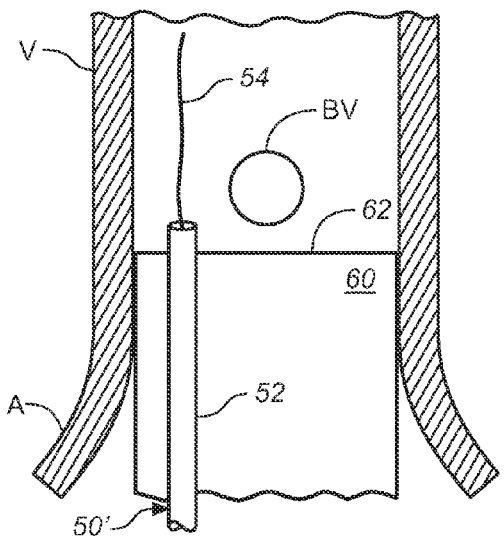
FIG. 4A
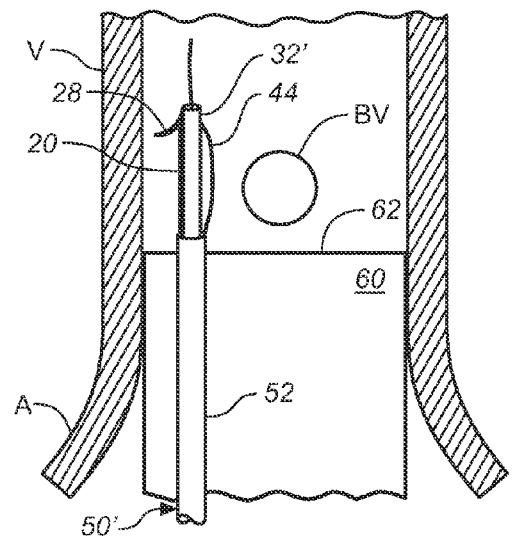
FIG. 4B
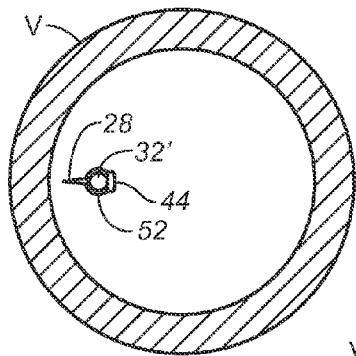
FIG. 4B1
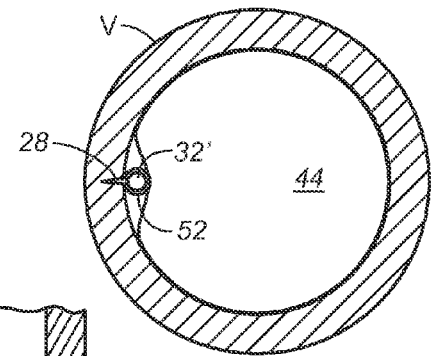
FIG. 4C1
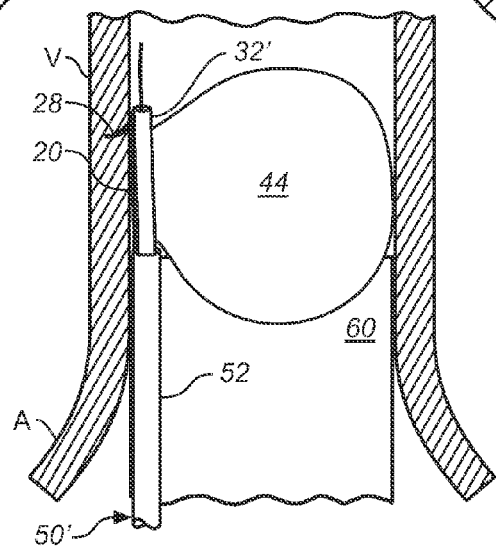
FIG. 4C

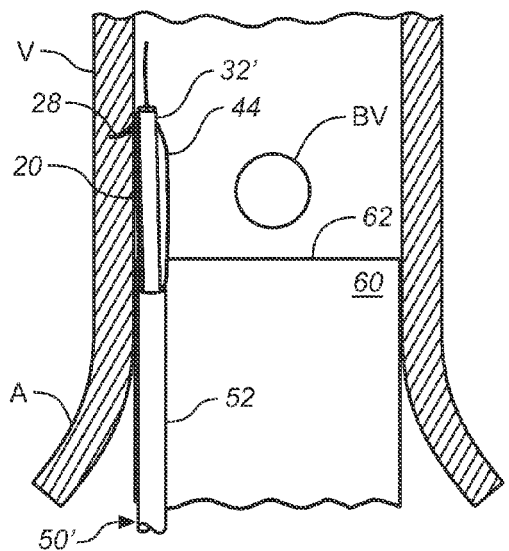
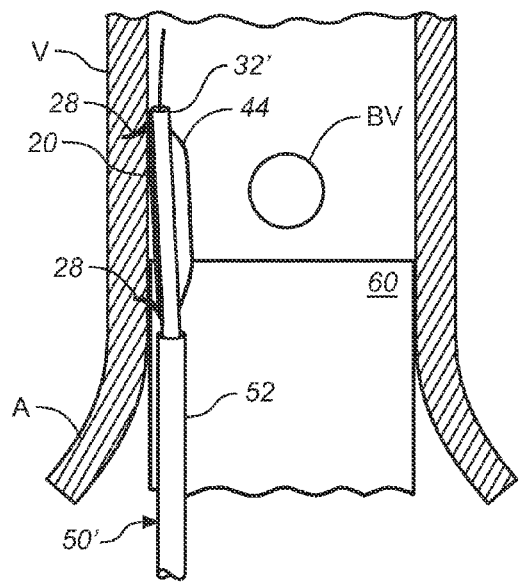
FIG. 4D  FIG. 4E
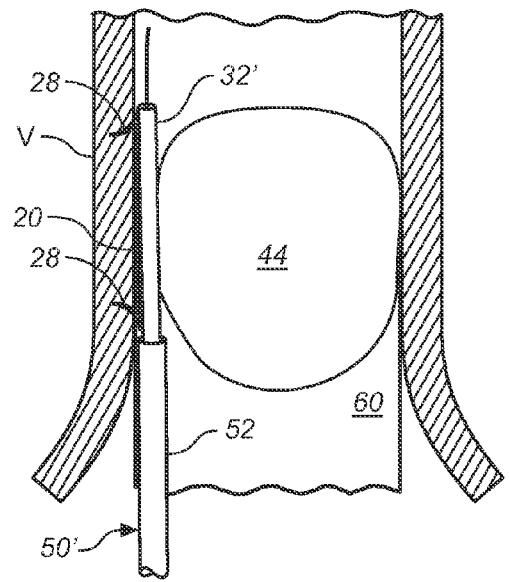
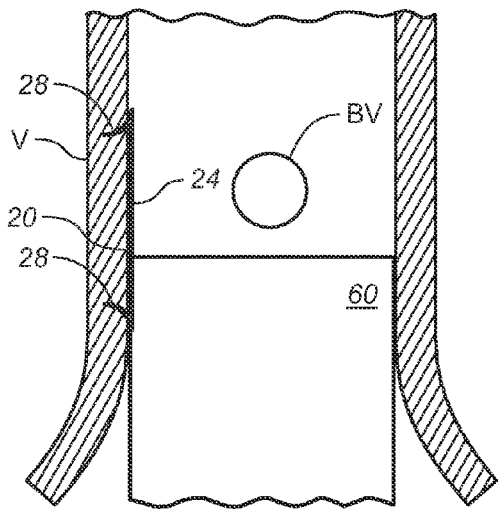
FIG. 4F  FIG. 4G

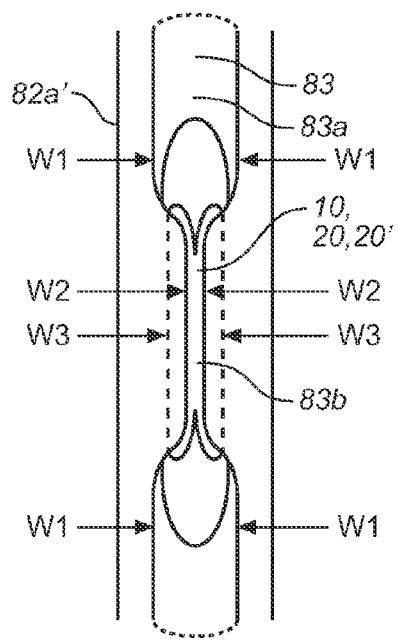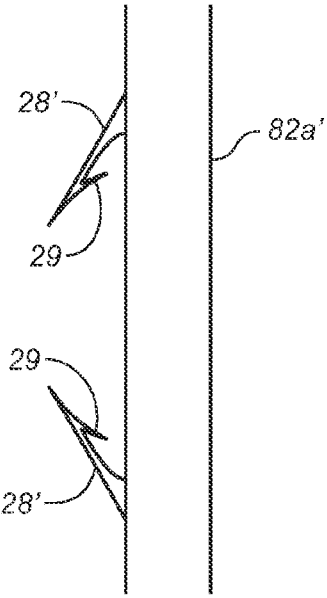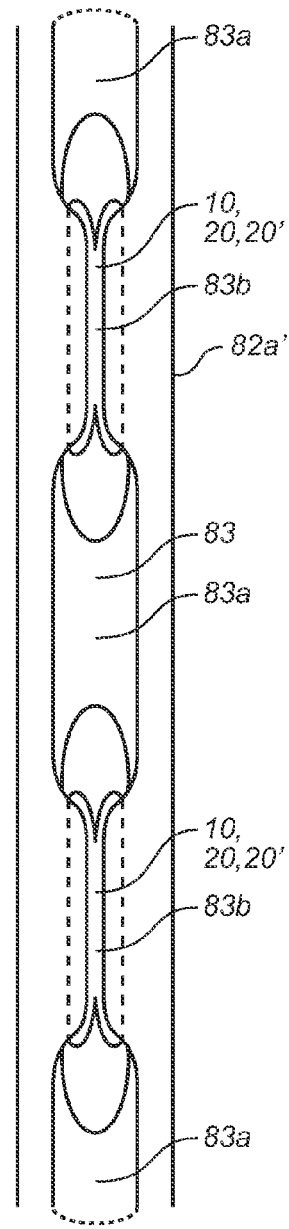
*FIG. 6D*　　*FIG. 6E*　　*FIG. 6F*

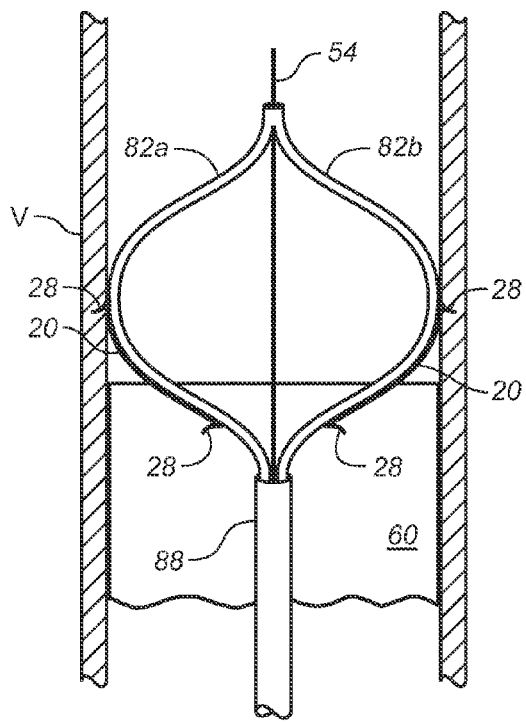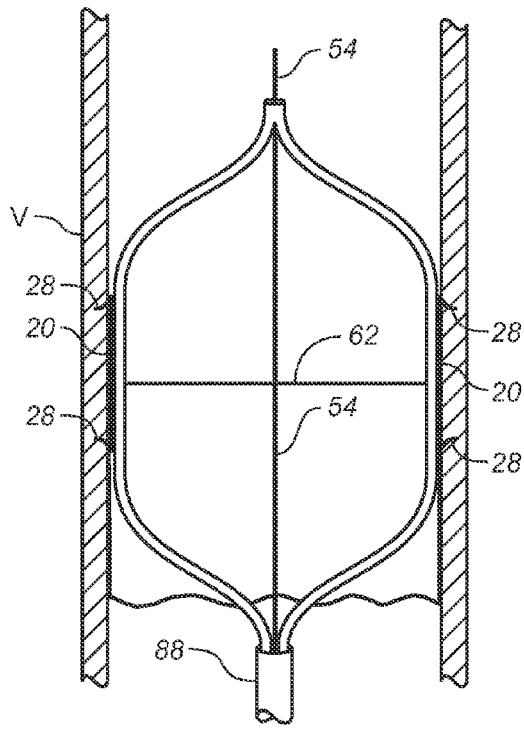
FIG. 8A  FIG. 8B
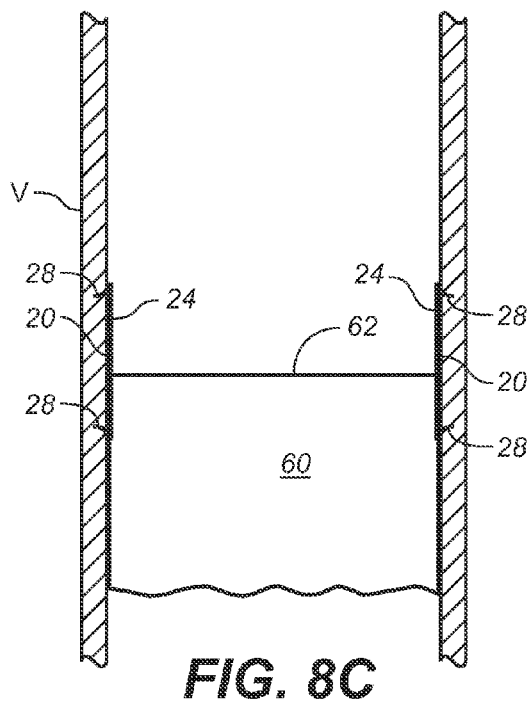
FIG. 8C

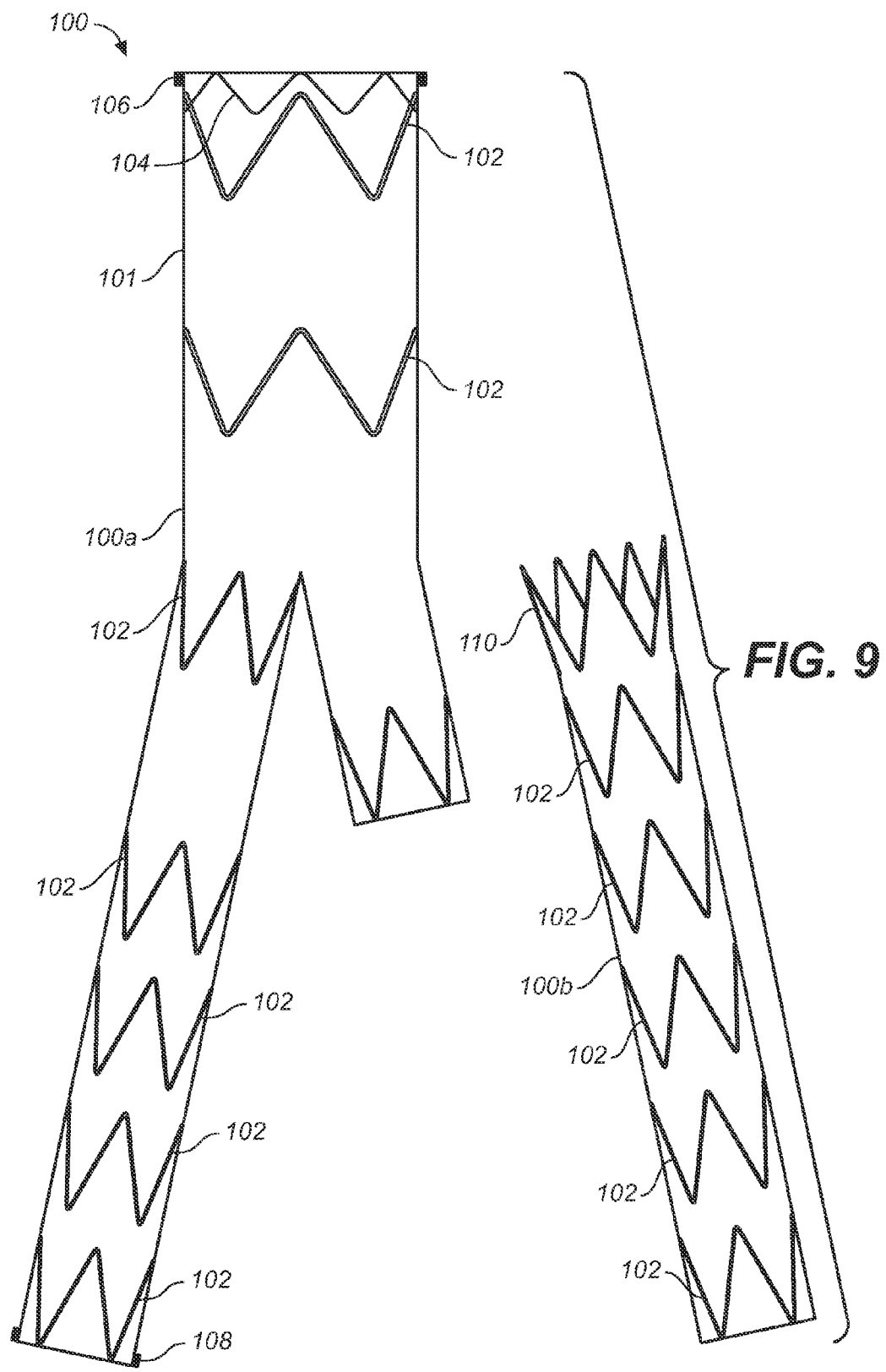

PROSTHESIS FIXATION APPARATUS AND METHODS

FIELD OF THE INVENTION

The invention relates to prosthesis fixation in a passageway in a human body such as an artery.

BACKGROUND OF THE INVENTION

Tubular prostheses such as stents, grafts, and stent-grafts (e.g., stents having an inner and/or outer covering comprising graft material and which may be referred to as covered stents) have been widely used in treating abnormalities in passageways in the human body. In vascular applications, these devices often are used to replace or bypass occluded, diseased or damaged blood vessels such as stenotic or aneurysmal vessels. For example, it is well known to use stent-grafts, which comprise biocompatible graft material (e.g., Dacron® or expanded polytetrafluoroethylene (ePTFE)) supported by a framework (e.g., one or more stent or stent-like structures), to treat or isolate aneurysms. The framework provides mechanical support and the graft material or liner provides a blood barrier.

Aneurysms generally involve abnormal widening of a duct or canal such as a blood vessel and generally appear in the form of a sac formed by the abnormal dilation of the duct or vessel wall. The abnormally dilated wall typically is weakened and susceptible to rupture. Aneurysms can occur in blood vessels such as in the abdominal aorta where the aneurysm generally extends below the renal arteries distally to or toward the iliac arteries.

In treating an aneurysm with a stent-graft, the stent-graft typically is placed so that one end of the stent-graft is situated proximally or upstream of the diseased portion of the vessel and the other end of the stent-graft is situated distally or downstream of the diseased portion of the vessel. In this manner, the stent-graft extends through the aneurysmal sac and beyond the proximal and distal ends thereof to replace or bypass the dilated wall. The graft material typically forms a blood impervious lumen to facilitate endovascular exclusion of the aneurysm.

Such prostheses can be implanted in an open surgical procedure or with a minimally invasive endovascular approach. Minimally invasive endovascular stent-graft use is preferred by many physicians over traditional open surgery techniques where the diseased vessel is surgically opened and a stent-graft is sutured into position such that it bypasses the aneurysm. The endovascular approach, which has been used to deliver stents, grafts and stent grafts, generally involves cutting through the skin to access a lumen of the vasculature. Alternatively, lumenar or vascular access may be achieved percutaneously via successive dilation at a less traumatic entry point. Once access is achieved, the stent-graft can be routed through the vasculature to the target site. For example, a stent-graft delivery catheter loaded with a stent-graft can be percutaneously introduced into the vasculature (e.g., into a femoral artery) and the stent-graft delivered endovascularly across the aneurysm where it is deployed.

When using a balloon expandable stent-graft, balloon catheters generally are used to expand the stent-graft after it is positioned at the target site. When, however, a self-expanding stent-graft is used, the stent-graft generally is radially compressed or folded and placed at the distal end of a sheath or delivery catheter. Upon retraction or removal of the sheath or catheter at the target site, the stent-graft self-expands. More specifically, a delivery catheter having coaxial inner and outer tubes arranged for relative axial movement therebetween can be used and loaded with a compressed self-expanding stent-graft. The stent-graft is positioned within the distal end of the outer tube (sheath) and in front of a stop fixed to the inner tube. Once the catheter is positioned for deployment of the stent-graft at the target site, the inner tube is held stationary and the outer tube (sheath) withdrawn so that the stent-graft is gradually exposed and allowed to expand. The inner tube or plunger prevents the stent-graft from moving back as the outer tube or sheath is withdrawn. An exemplary stent-graft delivery system is described in U.S. Patent Application Publication No. 2004/0093063, which published on May 13, 2004 to Wright et al. and is entitled Controlled Deployment Delivery System, the disclosure of which is hereby incorporated herein in its entirety by reference.

Although the endoluminal approach is much less invasive, and usually requires less recovery time and involves less risk of complication as compared to open surgery, there are concerns with fixation of the prosthesis and prosthesis migration. For example, the outward spring force of a self-expanding stent-graft may not be sufficient to prevent migration. This problem can be exacerbated when the vessel's fixation zone is not circumferential or it is calcified or when the proximal neck of an aneurysm, which extends toward the upstream branch vessel, is relatively short. And when treating blood vessel aneurysms, for example, migration can result in leakage of blood around the prosthesis and into the aneurysmal sac, which, in turn, can cause rupture of the dilated vessel wall. This problem is severe when the prosthesis is used to treat an aneurysm at or around the intersection of a major artery (e.g., the aorta) with the intersecting arteries (e.g., the renal, carotid or brachiocephalic arteries).

Other fixation mechanisms that reduce the chance of migration include mechanisms that comprise radially extending members such as tines, barbs, hooks and the like that engage the vessel wall. Still other attempts to improve the seal and/or fixation between the prosthesis and an endoluminal wall have included using adhesives and growth factor.

There remains a need to develop and/or improve seal and/or fixation approaches for endoluminal or endovascular prostheses placement.

SUMMARY OF THE INVENTION

The present invention involves improvements in prosthesis fixation and overcomes disadvantages of prior art.

In one embodiment according to the invention, a method of securing a prosthesis placed at a desired site in a passageway of a human body comprises delivering a fastener having a proximal piercing end portion and a distal piercing end portion to a site where a prosthesis having a tubular wall has been placed in the passageway, which has a wall; advancing the proximal piercing end portion beyond the prosthesis; penetrating the proximal piercing end portion into the wall of the passageway without passing the proximal piercing end portion through the tubular wall of the prosthesis; and passing the distal piercing end portion through the tubular wall of the prosthesis and into the wall of the passageway.

In another embodiment according to the invention, surgical fastener delivery apparatus for delivering a surgical fastener to a target site comprises a support having a first end, a second end, and a longitudinal axis and being adapted for placement in a passageway in a human body; a surgical fastener having a first piercing end portion, a second piercing end portion and a central portion extending therebetween and having a longitudinal axis. The fastener being releasably mounted to the support with the central portion longitudinal axis generally parallel to the support longitudinal axis.

In another embodiment according to the invention, surgical fastener delivery apparatus for delivering a surgical fastener to a target site comprises a support having a first end, a second end, and a longitudinal axis and being adapted for placement in a passageway in a human body; a surgical fastener having a first piercing end portion, a second piercing end portion and a central portion extending therebetween, the fastener being releasably locked to the support with the first piercing member being closer to the support first end as compared to the second piercing member; and a tubular sheath, the support being slidably disposed in the tubular sheath with the support and sheath being movable relative to one another such that the sheath covers the fastener piercing end portions when in a first position and the fastener piercing end portions extend from the sheath when the sheath is in a second position.

In another embodiment according the invention, a surgical fastener, such as a staple, for securing a prosthesis to a target site comprises a first V-shaped end portion having a free piercing end adapted to penetrate tissue; a second V-shaped end portion having a free piercing end adapted to penetrate tissue; and a flexible member having a first end attached to the first end portion and a second end attached to the second end portion.

In another embodiment according to the invention, a surgical fastener, such as a staple, for securing a prosthesis to a target site comprises a first V-shaped end portion having a prong adapted to penetrate tissue and an apex; a second V-shaped end portion having a prong adapted to penetrate tissue and an apex pointing in a direction generally opposite to the direction in which the first V-shaped end portion points; and a central portion interconnecting the V-shaped portions.

The above is a brief description of some deficiencies in the prior art and advantages of embodiments according to the present invention. Other features, advantages, and embodiments according to the present invention will be apparent to those skilled in the art from the following description and accompanying drawings, wherein, for purposes of illustration only, specific embodiments are set forth in detail.

BRIEF DESCRIPTION OF THE DRAWINGS

FIG. 1A is a front view of one embodiment of a prosthesis fixation device in accordance with the invention.

FIG. 1B is a side view of the device of FIG. 1A.

FIG. 1C is a rear view of the device shown in FIG. 1A.

FIG. 2A is a front view of another embodiment of a prosthesis fixation device in accordance with the invention.

FIG. 2B is a side view of the device of FIG. 2A.

FIG. 2C is a variation of the device of FIGS. 2A and 2B.

FIGS. 3A-D illustrate delivery apparatus for prosthesis fixation devices in accordance with the invention where, FIG. 3A illustrates delivery apparatus loaded with a plurality of fixation devices, each corresponding to that shown in FIG. 1A, FIG. 2B illustrates delivery apparatus loaded with a plurality of devices, each corresponding to that shown in FIG. 1B, FIG. 3C illustrates delivery apparatus as shown in either FIG. 1B or FIG. 2B and including an outer sheath, and FIG. 3D illustrates delivery apparatus with an expandable support.

FIGS. 4A-H diagrammatically illustrate prosthesis fixation in accordance with the invention where FIG. 4A illustrates positioning the delivery apparatus of FIG. 3D at a site, FIG. 4B illustrates advancing and exposing a proximal portion of a fixation device, FIG. 4B1 is a top view of FIG. 4B, FIG. 4C illustrates anchoring the proximal portion of the fixation device with a balloon that is integrated into the fixation device support of the delivery apparatus, FIG. 4C1 is a top view of FIG. 4C, FIG. 4D illustrates the proximal portion of the fixation device anchored and the balloon deflated, FIG. 4E illustrates exposing the distal portion of the fixation device, FIG. 4F illustrates anchoring the distal portion of the fixation device through the prosthesis with the balloon, FIG. 4G illustrates the fixation device securing the prosthesis in position and the delivery apparatus withdrawn, and FIG. 4H illustrates a second fixation device, which has been anchored at the site in a similar manner.

FIG. 5A illustrates exposing a proximal portion of a fixation device at a desired location with the delivery apparatus of FIG. 3C, FIG. 5B illustrates anchoring the proximal portion of the fixation device with a discrete expandable balloon, FIG. 5C illustrates exposing the distal portion of the fixation device with the balloon having been deflated and withdrawn, FIG. 5D illustrates anchoring the distal portion of the fixation device through the prosthesis with the balloon, which has been repositioned at the site and expanded, and FIG. 5E illustrates the prosthesis secured at the site with the fixation device anchored, the balloon having been deflated and withdrawn.

FIG. 6A is a front elevation view of the distal end portion of the apparatus in a partially extended and expanded state and with an optional fixation device shown in dashed line, FIG. 6B is a top view of the apparatus of FIG. 6A taken along line 6B-6B with optional arms shown in dashed line, and FIG. 6C illustrates the delivery apparatus support shown in FIG. 6A without the retaining sheath and in a fully expanded free state.

FIG. 6D is a side view of a portion of the apparatus of FIG. 6A illustrating one embodiment of a releasable locking mechanism.

FIG. 6E is another view of the portion depicted in FIG. 6D rotated 90 degrees.

FIG. 6F is another embodiment of the apparatus of FIG. 6A having a plurality of serially aligned fixation devices.

FIG. 7A illustrates positioning the delivery apparatus at the site, FIG. 7B illustrates exposing the proximal end of a fixation device; FIG. 7C illustrates further expanding the delivery apparatus fixation device support, FIG. 7D illustrates further support expansion to anchor the proximal portion of the fixation device, FIG. 7E illustrates the support expanded to anchor the distal portion of the fixation device in the prosthesis and vessel wall, and FIG. 7F illustrates the prosthesis secured with fixation device and the delivery apparatus withdrawn.

FIG. 8A-C illustrate deployment of a plurality of fixation devices simultaneously with the delivery apparatus of FIG. 6A, where FIG. 8A illustrates both fixation devices exposed with the proximal portions anchored, FIG. 8B illustrates both fixation devices anchored, and FIG. 8C illustrates the prosthesis secured with the fixation devices and the fixation device delivery apparatus withdrawn.

FIG. 9 illustrates one embodiment of the prosthesis illustrated in FIG. 4H.

DETAILED DESCRIPTION

Figure 4H:
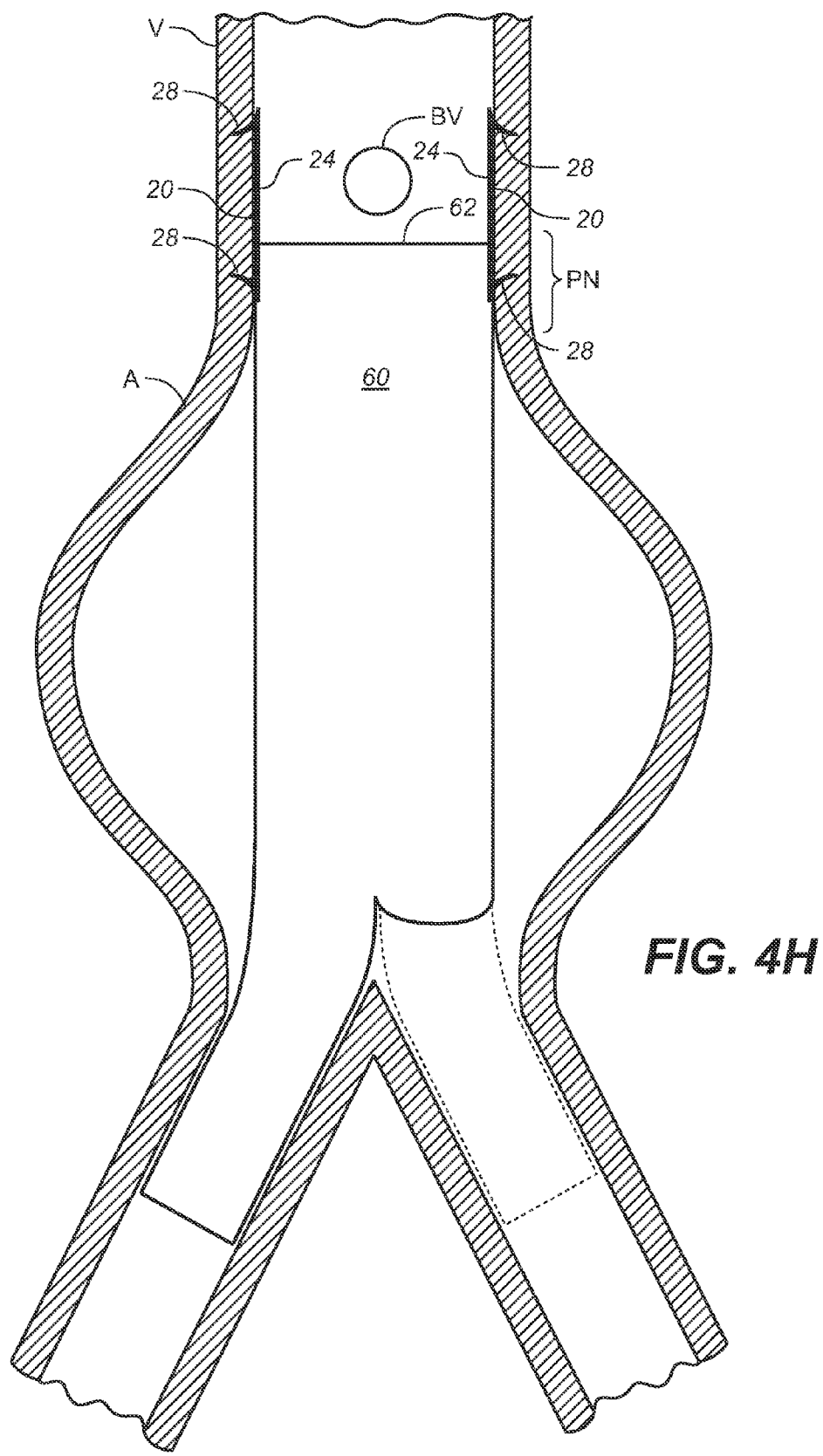

The following description will be made with reference to the drawings where when referring to the various figures, it should be understood that like numerals or characters indicate like elements.

Generally speaking, the proximal end of the prosthesis and fastener generally are referred to as the ends closest to the heart during deployment. In contrast, the proximal end of the catheter or delivery device is the end nearest the operator, the distal end generally being that which is farthest from the operator. However, the stent graft and delivery system description may be consistent or opposite with this depending on the access location.

One embodiment generally involves apparatus and methods for prosthesis fixation, the apparatus comprises a surgical fastener having one end that passes through the prosthesis and into tissue that interfaces with an outer surface of the prosthesis and another end that is beyond the prosthesis and is secured to tissue without passing through the prosthesis. This approach can be especially advantageous when the prosthesis is to be placed in the vicinity of a branch passageway. For example, when bypassing an abdominal aortic aneurysm with a stent-graft where there is insufficient proximal neck (e.g., less than about 1 cm) between the aneurysm and the renal arteries, the proximal portion of the prosthesis can still be positioned along the proximal neck and the fastener anchored in a manner so as to bridge the area between the prosthesis proximal portion and a portion of the aorta upstream of the renal arteries where one end of the proximal end of the fastener can be secured to the arterial wall. This anchoring approach avoids covering the access to the renal arteries with the stent-graft. Further, one or more fasteners can be deployed at the site. When a plurality of fasteners are deployed, they can be deployed either sequentially or simultaneously as will be described in more detail below.

Referring to FIGS. 1A-C, a first embodiment of a surgical fastener or fixation device in accordance with the invention is shown and generally designated with reference numeral 10. Fastener or fixation device 10 comprises V-shaped end portions 12 and a connecting portion 14 having a first end secured to an end of one of the V-shaped portions 16 and another end secured to the other V-shaped portion 12. The attachment can be made in any suitable manner. For example, the attachment end portion of each V-shaped portion can have an opening formed therein and the ends of connecting portion 14 passed therethrough and tied off or the V-shaped portions crimped or swaged. Alernatively, the ends of connecting portion or member 14 can be glued to the V-shaped end portions. In the illustrative embodiment, connecting portion 14 is a flexible member and can comprise any suitable material to provide the desired flexibility to conform to tortuous anatomy. Connecting member 14, for example, can be a thread, suture or wire. V-shaped end portions 12 each include an inner leg 16 and outer leg 18 which form an apex 17. The fastener portion between apices 17 may be referred to as the central or bridging portion. In the illustrative embodiment, each outer leg 18 includes a piercing end portion with a pointed tip and may be referred to as a prong. Each V-shaped apex 17 forms an axial end of fastener 10 and each leg 18 generally extends inwardly from an axial end toward the other leg of the fastener.

Referring to FIGS. 2A and 2B, another fastener or fixation device is shown and generally indicated with reference numeral 20. Fastener or fixation device 20 includes legs 28, which extend from the ends of connecting portion 24. In the illustrative embodiment, each leg has a piercing end portion with a pointed tip and may be referred to as a prong. Each leg and a portion of connecting portion 24 forms a V-shaped portion 22. Each V-shaped portion forms an apex 27, which forms an axial end of fastener 20, and each leg 28 generally extends inwardly from an axial end toward the other leg of the fastener. The fastener portion between apices 27 may be referred to as a central or bridging portion.

Referring to FIG. 2C, a variation is shown and generally designated with reference numeral 20'. Fastener or fixation device 20' is the same as fastener or fixation device 20 with the exception that fastener 20' includes barbs. More specifically, fastener 20' includes legs 28', which are the same as legs 28 with the exception that each leg 28' includes at least one barb 29 extending from the inner portion of the leg ends toward central portion 24. The distal barb, which is the one placed downstream in a vessel, can minimize or eliminate the risk of the prosthesis falling off the fastener. When the distal barb is pushed into a vessel wall (e.g., when the prosthesis is placed in a vessel), the barb further anchors the prosthesis to protect against migration. Although each leg 28' is shown with a single barb, either one or both legs can be provided with a plurality of barbs.

V-shaped portions 12 of fastener 10 and fasteners 20 and 20' can be made from plastic such as nylon or polyurethane or any suitable metal such as nitinol or stainless steel. The material is selected so that legs 18, 28 or 28' can be bent inwardly toward central portion 14 or 24 when loaded in a sheath or catheter, as will be described below, and then return to the their preshaped configuration, as shown in FIGS. 1A-C and 2A-C, when deployed. These fasteners can be made (e.g., cut from nitinol material, bent and heat treated. The length L of the bridging portion of the fastener, which corresponds to the distance from one apex to the other, varies depending upon the application. Typically, length L will be about 2-3 cm when anchoring an abdominal aortic aneurysmal (AAA) graft or stent graft. The length of each prong also may vary and typically will be about 2 to 5 mm. The width of fastener 20 or 20' typically will be about 0.25 to 2 mm and its thickness about 0.25 to 2 mm. Although various fastener configurations have been described, other configurations can be used without departing from the scope of the invention. For example, the V-shaped portions can be U-shaped or L-shaped and the ends of the bridging or central portion rounded.

Referring to FIGS. 3A-D, an exemplary fastener delivery apparatus will be described. In FIG. 3A, a first delivery apparatus is shown and generally designated with reference numeral 30. Delivery apparatus 30 includes a support 32, which can be a tubular member, which is flexible and suitable for endovascular delivery to the desired site i.e., a catheter, and a plurality of fasteners 10 releasably secured thereto.

Referring to FIG. 3B, another delivery apparatus is shown and generally designated with reference numeral 40. Delivery apparatus 40 is the same as delivery apparatus 30 with the exception that delivery apparatus 40 includes a plurality of fasteners 20, 21' releasably secured to support 32.

The fasteners 10, 20 or 20' (fastener 20' is not shown for purposes of simplification) also each have a longitudinal axis that is generally parallel to the longitudinal axis of support 32. Alternatively speaking, each fastener has a proximal piercing end (the end that will face fluid flow when implanted) that is closer to the support distal end (the end that is endoluminally introduced to the target site) as compared to the fastener's distal piercing end. The piercing end portions extend generally radially outward from the support (see e.g., FIGS. 3C and 4E).

Although three fasteners are shown coupled to support 32 in FIGS. 3A and 3B, it should be understood that one more fasteners can be releasably secured to support 32 depending on the application. Thus, for example, 1, 2, 3, 4, 5, 6, 7, 8, 9 or 10 fasteners can be releasably secured to support 32. They can be either serially aligned or circumferentially spaced or a combination of both. The plurality of fasteners facilitates deployment of one or more fasteners at the first prosthesis site and allows the surgeon to deploy one or more fasteners at a second prosthesis site without the need to completely withdraw and reload the delivery apparatus. Small amounts of biomedical adhesive glue can be applied intermittently along the back of the V-shaped portions to releasably secure a given fastener to support 32. The adhesive prevents relative axial movement between the fasteners and the support until the fastener is pulled from the support and the adhesive lock therebetween released as will be described in more detail below.

Referring to FIG. 3C, another embodiment of a delivery apparatus according to the invention is shown and generally designated with reference numeral 50. Delivery apparatus 50 includes either apparatus 30 or 40 and a tubular sheath 52, which surrounds either apparatus 30 or 40. Sheath 52 and whichever apparatus 30 or 40 disposed therein are axially slidably relative to one another so that the fasteners can be controllably and selectively exposed at the target site. Sheath 52 can be sized so that its inner wall elastically deforms and/or restrains the piercing portions of the fasteners radially inward so as to minimize the apparatus profile during delivery.

Referring to FIG. 3D, another delivery apparatus is shown and generally designated with reference numeral 50'. Delivery apparatus 50' is the same as delivery apparatus 50 with the exception that the fastener support 32' differs. Fastener support 32' is the same as fastener support 32 with the exception that fastener support 32' includes a radially expandable member associated or aligned with each fastener. In the illustrative example, the radially expandable member is balloon 44. Each balloon is sized so that when inflated, it will press the fastener firmly to the wall, and typically will around the support. Fluid channel 46 can be provided in the wall of catheter or support 32' and fluidly coupled to balloon 44 as shown in the uppermost balloon of FIG. 3D. Similar channels, which are hidden from view, are circumferentially spaced from the illustrated channel 46 so as to provide independent inflation control of each balloon. The channels extend to the proximal end of catheter or support 32' where they are fluidly coupled to a pressure or fluid source in a conventional manner. Each balloon can be adhesively secured to the support in a conventional manner. Further, although three balloons are shown, it should be understood that number of balloons typically will correspond to the number of fasteners, which as described above can vary. Thus, for example, 1, 2, 3, 4, 5, 6, 7, 8, 9 or 10 balloons can be secured to support 32.

Referring to FIGS. 4A-H, one example method of fixing a prosthesis at a desired site will be described. It should be understood, however, that this example is not intended to limit the scope of the invention, but merely is provided for illustrative purposes.

In this example, the proximal portion of a bifurcated prosthesis is secured to the portion of a vessel distal to a branch vessel and along the proximal neck between an aneurysm and the branch vessel upstream therefrom. FIG. 4A illustrates prosthesis 60, which is a bifurcated prosthesis (see FIG. 4H), deployed at the desired site with its proximal end 62 positioned below branch vessel BV. As shown in FIG. 4A, it is positioned in vessel V, which can be the aorta of a patient, to bypass an aneurysm A, which is situated below branch vessel BV, which can be a renal artery. The proximal end portion of the prosthesis can be provided with a member to exert a force against the inner wall of the proximal neck PN of the vessel (see FIG. 4H) so as to secure the prosthesis in the desired position before the fixation device is deployed. Such a member can work with one or more of the fixation devices described herein to secure the prosthesis to the vessels. One suitable member is an annular undulating wire spring as shown in FIG. 9 and indicated with reference numeral 102.

Any suitable delivery catheter can be used to endovascularly deliver the prosthesis to the desired site. When the prosthesis is a self-expanding graft or stent-graft, it generally is radially compressed or folded and placed at the distal end of a sheath or delivery catheter and allowed to expand upon deployment from the sheath or catheter at the target site. More specifically, a delivery catheter having coaxial inner and outer tubes arranged for relative axial movement therebetween can be used and loaded with a radially compressed self-expanding prosthesis (e.g., self-expanding stent-graft). The prosthesis is positioned within the distal end of the outer tube (sheath) and in front of the inner tube (plunger). The catheter is routed through the vasculature to the desired site. Once the catheter is positioned for deployment of the prosthesis at the desired site, the plunger is held stationary and the outer tube or sheath withdrawn so that the stent-graft is gradually exposed and allowed to expand. The plunger prevents the stent-graft from moving back as the sheath is withdrawn. Any of the stent-graft delivery systems described in U.S. Patent Application Publication No. 2004/0093063, which published on May 13, 2004 to Wright et al. and is entitled Controlled Deployment Delivery System, the disclosure of which is hereby incorporated herein in its entirety by reference, can be used as well.

After the prosthesis has been deployed and the prosthesis delivery catheter withdrawn, fastener delivery apparatus 50 is endovascularly delivered to the site with its distal end in the vicinity of the proximal portion of the prosthesis. Apparatus 50 can be introduced into the vasculature percutaneously through, for example, one of the femoral arteries and delivered to the target site over a guidewire 54, which can be the same guidewire used to guide the prosthesis delivery catheter to the site.

Referring to FIGS. 4B and 4B1, the surgeon holds sheath 52 fixed and pushes support tube 32' to advance the distal end of the support tube above branch vessel BV and expose the proximal end of fastener 20 including one of prongs 28. After the prong is positioned upstream of branch vessel BV, balloon 44 is inflated to push the proximal prong into the vessel wall and anchor the proximal portion of the fastener as shown in FIGS. 4C and 4C1. With the proximal portion of the fastener anchored, the balloon is deflated (FIG. 4D) and sheath 52 withdrawn while support tube 32' is held stationary to expose the distal prong of fastener 20 (FIG. 4E). Balloon 44 again is inflated to push the distal prong through the wall of prosthesis 60 and into the vessel wall to secure the prosthesis to the fastener and anchor the distal portion of the fastener to the vessel FIG. 4F. After the fastener is secured in place as shown in FIG. 4F, the fastener balloon 44 is deflated again and the delivery apparatus withdrawn (FIG. 4G). However, if the surgeon desires to place a second fastener in the vessel at a location diametrically opposed to the first fastener as shown FIG. 4H, the delivery apparatus need not be withdrawn. It is simply rotated about 90 degrees and moved close to the other side of the vessel and the procedure described above repeated. After rotation, the support can be extended and the balloon inflated to move the support to the other side. It should be understood that more fasteners can be deployed as well. However, two, three or four fasteners typically will be used. They can be equiangularly spaced in a circumferential direction or the circumferential distance between the fasteners can vary depending on the application and accessibility of tissue suitable for holding a respective fastener.

Figure 5A:
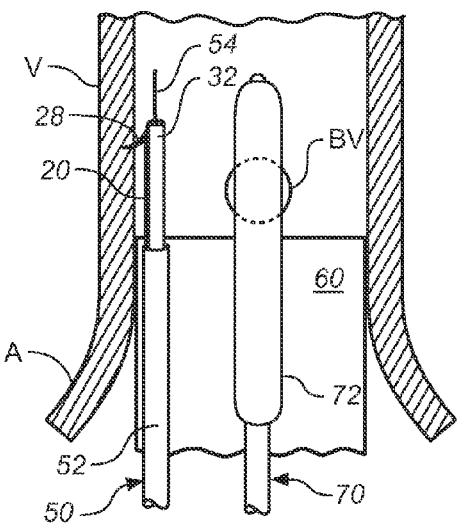
FIGS. 5A-E diagrammatically illustrate another method of prosthesis fixation, where
Figure 5B:
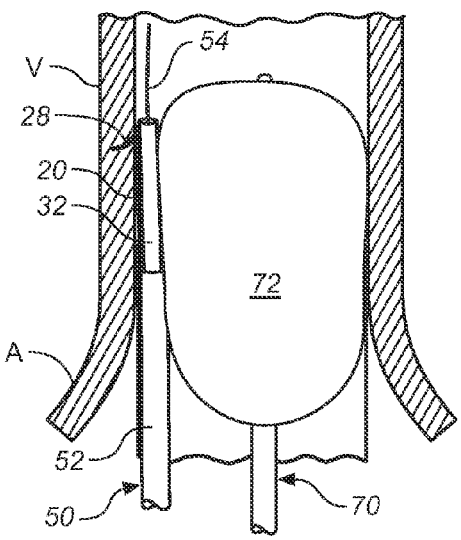
Figure 5C:
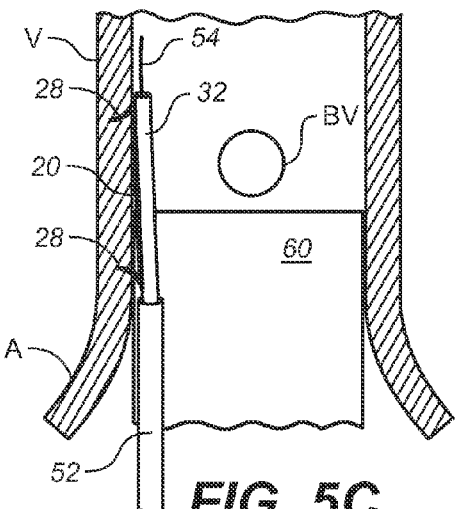
Figure 5D:
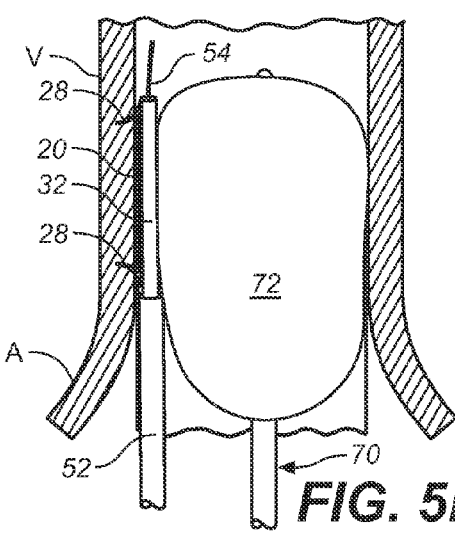
Figure 5E:
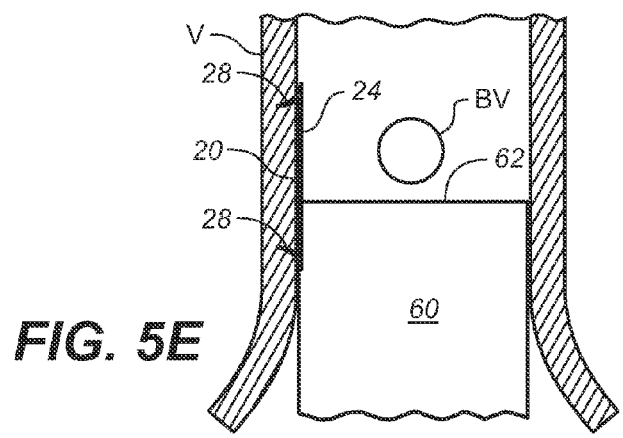

FIGS. 5A-E diagrammatically illustrate another method of prosthesis fixation using a system comprising delivery apparatus 50 and a discrete balloon catheter 70 of traditional construction and having a 360 degree expandable balloon. Referring to FIG. 5A, delivery apparatus 50 has been guided over guidewire 54 to the desired location in the vicinity of the proximal end of prosthesis 60. Balloon catheter 70 also has been routed through the vasculature over a guidewire (not shown) to the position shown. Support tube 32 has been advanced while sheath 52 held stationary to expose the proximal prong of fastener 20 as described above in connection with the FIG. 4B and the prong urged against the inner wall of vessel. Balloon 70 is then inflated so that it expands and pushes or forces the proximal prong of the fastener into the vessel wall to anchor the proximal portion of the fastener therein (FIG. 5B). Balloon 72 is deflated and may or may not be withdrawn as sheath 52 is withdrawn while holding support tube 32 to expose the distal portion of the fastener (FIG. 5C). Balloon 72 is positioned as shown in FIG. 5D and inflated again to expand and push or force the distal prong through the wall of prosthesis 60 and into vessel V. The balloon is then deflated and withdrawn leaving fastener 20 in place and spanning the portion of the vessel between the proximal portion of prosthesis 60 and the portion of vessel V proximal to branch vessel BV (FIG. 5E). In other words, fastener 20 bridges the proximal end portion of the prosthesis to the vessel area above branch vessel BV. If desired, one or more additional fasteners can be deployed to bridge the same region at circumferentially spaced locations using the same procedure.

Figure 6A:
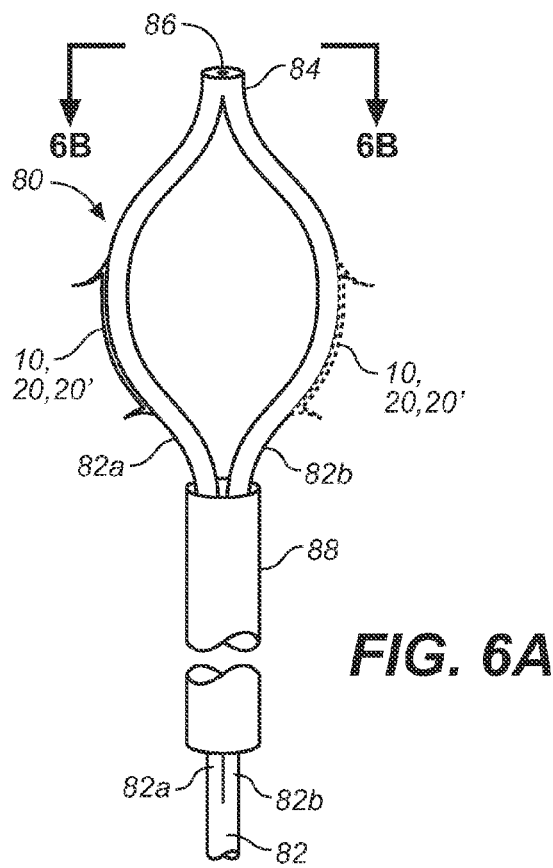
FIGS. 6A-C illustrate another fixation device delivery apparatus, where
Figure 6B:
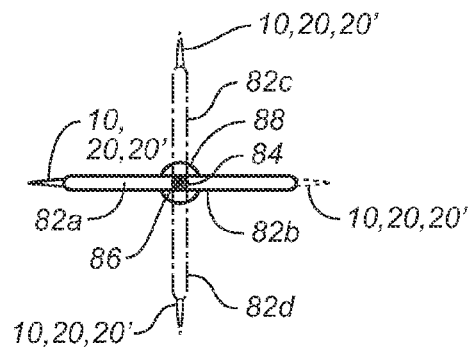

FIGS. 6A-B illustrate another fastener delivery apparatus embodiment which is generally designated with reference numeral 80. Referring to FIG. 6A, delivery apparatus 80 includes fastener support 82 and tubular sheath 88, which surrounds support 82. Fastener support 82 is slidably disposed in tubular sheath 88 so that they are slidably movable relative to one another. Support 82 has a proximal portion comprising a member that splits into elongated arms 82a and 82b. One or more fasteners 10, 20 or 20' can be releasably attached one or both arms 82a and 82b. In FIG. 6A, an optional fastener for arm 82b is shown in dashed line. The distal portions of arms 82a and 82b rejoin to form the distal portion of support 82, which is designated with reference numeral 84. An axial opening 86 is formed through distal portion 84 and the proximal portion of support 82. The openings are sized so that a guidewire can be slidably disposed therein (or guided by an optional guidewire lumen not shown) and extend from both ends thereof. In this manner, a guidewire can endovascularly guide the delivery apparatus to the desired site (see e.g., FIGS. 7A and B).

Although a two arm configuration is shown in FIG. 6A, other multiples of arms can be used. For example, support 82 can include 2, 3, 4, 5 or 6 arms. FIG. 6B is a top view of the apparatus of FIG. 6A taken along line 6B-6B with optional arms showing additional arms in dashed line and designated with reference numerals 82c and 82d. Fasteners 10, 20 or 20' (fastener 20' is not shown for purposes of simplification) each have a longitudinal axis that is generally parallel to the longitudinal axis of support 32. Alternatively speaking, each fastener has a proximal piercing end (the end that will face fluid flow when implanted) that is closer to the support distal end (the end that is endoluminally introduced to the target site) as compared to the fastener's distal piercing end. The piercing end portions extend generally radially outward from the support (see e.g., FIGS. 3C and 4E).

Generally speaking, one or more fasteners can be releasably secured to support 82 depending on the application. Thus, for example, 1, 2, 3, 4, 5, 6, 7, 8, 9 or 10 fasteners can be releasably secured to support 82. Further, although one fastener is shown coupled to support arm 82a and an optional fastener coupled to support arm 82b, other configurations can be made without departing form the scope of the invention. For example, a support can have four arms 82a, 82b, 82c and 82d as shown in FIG. 6B and each arm provided with three serially aligned fasteners. Other combinations will be readily apparent to one skilled in the art.

The plurality of fasteners facilitates deployment of one or more fasteners at the first prosthesis site and allows the surgeon to deploy one or more fasteners at a second prosthesis site without the need to completely withdraw and reload the delivery apparatus.

Small amounts of biomedical adhesive glue can be applied intermittently along the back of the fastener V-shaped portions to releasably secure a given fastener to support 82. The adhesive prevents relative axial movement between the fasteners and the support until the fastener is pulled from the support and the adhesive lock therebetween released as will be described in more detail below.

Figure 6C:
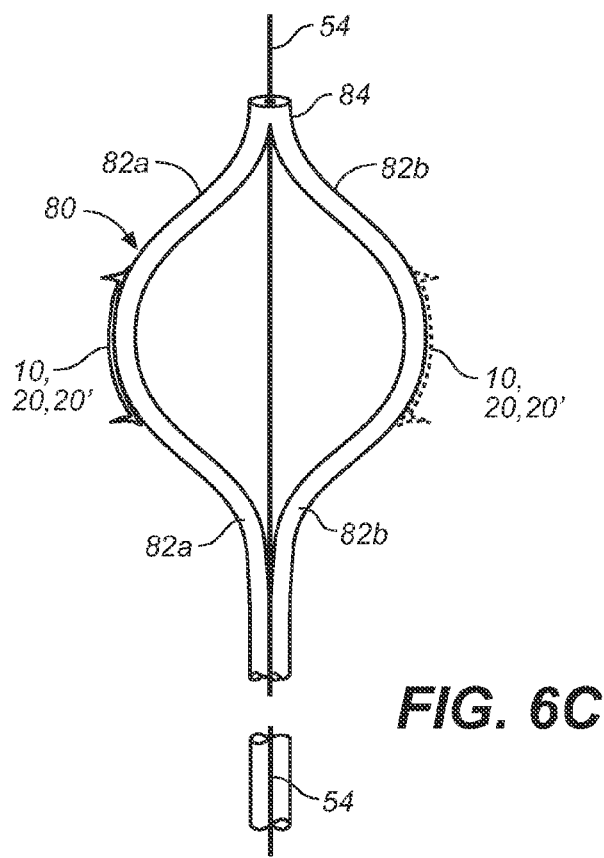

Referring to FIG. 6C, the two arm configuration of FIG. 6A is shown without sheath 88 and in an unrestrained configuration where the arms exhibit their preshaped configuration. More specifically, each support arm has a preshaped or memory set curved configuration so that together arms 82a and 82b form a generally eliptical shape as shown in FIG. 6C. The preshaped configuration can have a larger diameter or have a more oblong shape when a plurality of fasteners are serially aligned along either or both arms to accommodate radial displacement of each fastener as one moves proximally along the delivery apparatus. The radius of each arm in its relaxed or free state can be the same as the other to facilitate centering the apparatus in a lumen such as a vessel as will be described in more detail below.

When sheath 88 is advanced over the distal end portion of support 82, it restrains the elongated arms 82a and 82b in a closed deformed shape. This reduces the apparatus profile when its distal end is delivered endovascularly to the desired site. The sheath also protects the lumen walls from the fastener piercing end portions. When the distal portion of the apparatus is at the desired site, the support and/or sheath can be manipulated to expose a distal portion of the support so that the elongated arms 82a and 82b tend to move toward or return to their preshaped configuration as shown in FIG. 6A and urge the fasteners radially outward and toward the inner wall of the lumen or vessel. Accordingly, the elongated arms can be referred to as self-expanding members.

Arms 82a and 82b can be of any suitable material. For example, arms 82a and 82b (or support 82) can be nitinol and can be placed in the desired shape (e.g., that shown in FIG. 6C) and heated for about 5-15 minutes in a hot salt bath or sand having a temperature of about 480-515° C. They can then be air cooled or placed in an oil bath or water quenched depending on the desired properties. In one alternative, arms 82a and 82b (or support 82) can be surgical grade stainless steel that is deformed to assume such a preshaped configuration. In a further embodiment, the arms or support 82 can be a polymer.

FIG. 6D is a side view of a portion of the apparatus of FIG. 6A where the fastener positioned, illustrating a variation of the releasable locking mechanism. In this embodiment, the fastener is releasably retained in a groove as compared to the adhesive approach described above. Elongated member 82a' is the same as member 82 with the exception that member 82a' has a recessed wall that forms channel 83 and a channel opening. In the illustrative embodiment, the channel extends generally parallel to the longitudinal axis of the support arm. The channel can terminate close to where the proximal and distal ends of the fastener are seated as shown in dashed line.

The channel may extend further (e.g., more length makes fastener release easier when bent).

The channel opening also has a first portion having a width W1, which is followed by a second portion having a width W2, which is followed by another portion having a width W1, where W1 is greater than W2. The fastener is seated in the channel with each piercing end portion abutting the channel wall at the juncture of where the opening narrows to the portion having a width of W2. This axially locks the clip and prevents relative axial movement between the fastener and the support arm. The portion of the fastener between the piercing end portions has a width greater than W2 and can generally correspond to width W1. In this manner, the fastener is releasably retained in the channel. When the arm is allowed to move toward its preshaped curved configuration and its radius of curvature allowed to increase, the hoop stress will cause W2 to progressively enlarge and allow release of the fastener. FIG. 6E shows the portion of arm 82a' rotated 90 degrees.

FIG. 6F is another embodiment of the apparatus of FIG. 6C having a plurality of serially aligned fasteners, each releasably retained in channel 83 in the same manner as described above in connection with FIG. 6C.

Figure 7A:
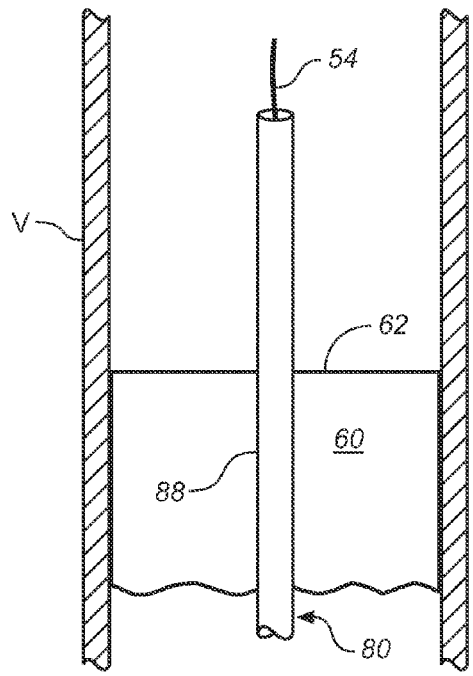
FIGS. 7A-F illustrate deployment of a fixation device with the delivery apparatus of FIG. 6A where
Figure 7B:
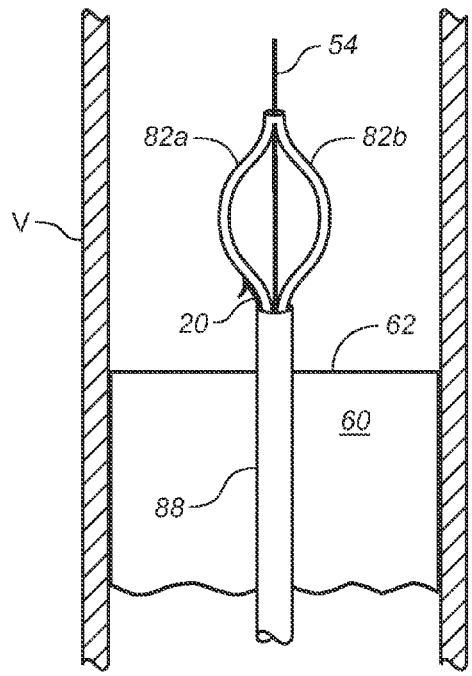
Figure 7C:
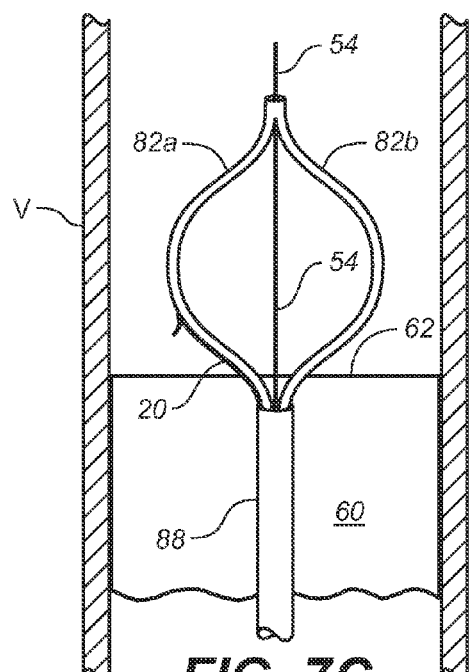
Figure 7D:
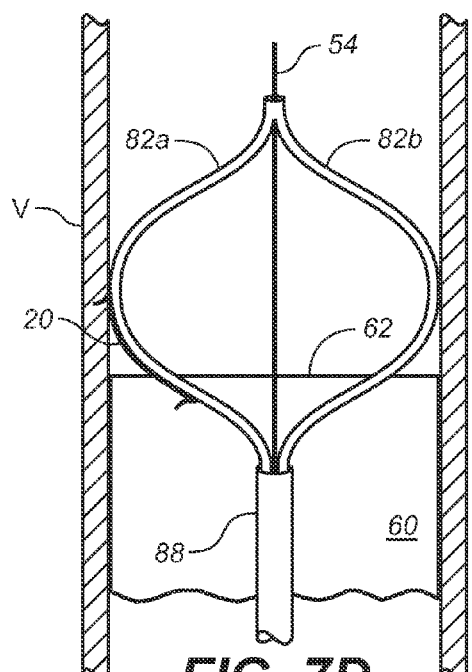

FIGS. 7A-F illustrate deployment of a fixation device with the delivery apparatus of FIG. 6A. After prosthesis 60 has been deployed and the prosthesis delivery catheter withdrawn, fastener delivery apparatus 80 is endovascularly delivered to the site with its distal end above proximal end 62 of prosthesis 60 as shown in FIG. 7A. Apparatus 80 can be introduced into the vasculature percutaneously through, for example, one of the femoral arteries and delivered to the target site over a guidewire 54. Once the apparatus is so positioned, the surgeon holds support 82 stationary and withdraws sheath or catheter 88 to expose support arms 82a and 82b and expose the proximal end of fastener 20 including one of prongs 28 (FIG. 7B). The surgeon continues to withdraw sheath 88 and progressively allow support arms 82a and 82b to radially expand (FIG. 7C). As sheath 88 is further withdrawn, arm 82a forces or pushes the proximal prong of fastener 20 into the wall of vessel V to anchor the proximal portion of the fastener while exposing the distal prong of fastener 20 (FIG. 7D). Arm 82b being in contact with the vessel wall provides a foundation from which arm 82a can push. When using the release mechanism of FIG. 6D, it is noted that at this point the radius of curvature arm 82a in the area of proximal portion of the fastener is large enough to cause that portion to be released. As both arms contacting diametrically opposed portions of the vessel wall, they also work to center the apparatus in the vessel lumen. The catheter or sheath 88 may be manipulated as needed to assure secure engagement.

Figure 7E:
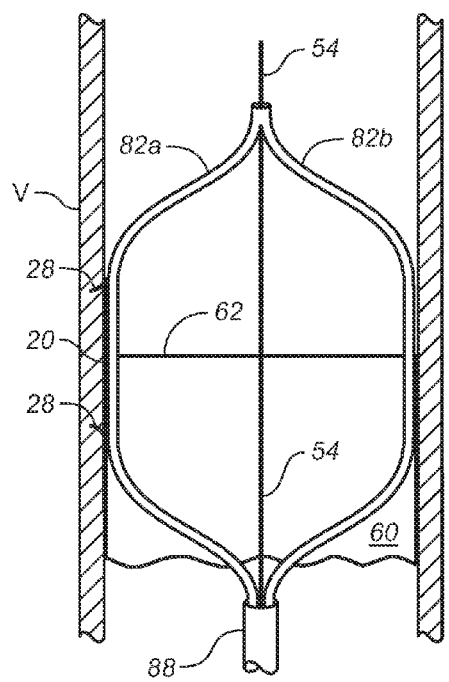
Figure 7F:
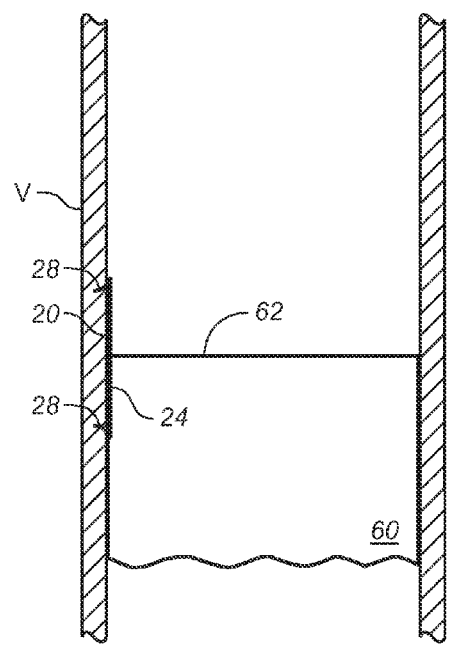

Catheter or sheath 88 is then further withdrawn while arms 82a and 82b are held stationary to allow the arms to further radially expand and push the distal prong of the fastener through the wall of prosthesis 60 and into the vessel wall to secure the prosthesis to the fastener and anchor the distal portion of the fastener to the vessel FIG. 7E. The vessel wall tends to restrain arms 82a and 82b from returning to the preshaped configuration shown in FIG. 6C and tends to flatten the fastener seating portions of the arms as shown in FIG. 7E. Again, when using the release mechanism of FIG. 6D, it is noted that the distal prong approaches the vessel wall, the radius of curvature of the support arm in that region sufficiently increases to widen channel opening W2 and release the fastener. After the fastener is secured in place as shown in FIG. 7E, the surgeon holds arms 82a and 82b stationary and advances sheath 88 to force the arms radially inward and into the sheath. The sheath and support are then withdrawn leaving the fastener, which fixes the prosthesis to the vessel wall as shown in FIG. 7F. When the fastener is adhesively secured to support arm 82a, the support arms are withdrawn while in the configuration of FIG. 8B to release the fastener. Then the arms are withdrawn back into sheath 88 and removed therewith.

FIGS. 8A-C illustrate deployment of a plurality of fixation devices simultaneously with the delivery apparatus of FIG. 6A. In this embodiment, a fastener is releasably secured to arm 82a and 82b. The apparatus is delivered to the desired site and the proximal prongs exposed as described above. Sheath 88 is progressively withdrawn so that the proximal prongs are pushed into the vessel wall (FIG. 8A) and then the distal prongs are pushed into the vessel wall (FIG. 8B). After the anchored fasteners have been released from channel 83 as described above, the surgeon holds arms 82a and 82b stationary and advances sheath 88 to force the arms radially inward and into the sheath and then withdraws the sheath and support.

Referring to FIG. 9, one embodiment of the prosthesis of FIG. 4H is shown and generally designated with reference numeral 100. Prosthesis 100 is a bifurcated stent-graft having a modular construction, which includes portions 100a (having and ipsilateral leg portion) and 100b (the contralateral leg portion) to facilitate delivery and deployment at a bifurcated passageway such as where the aorta branches to the iliac arteries. The contralateral leg portion 100b can be coupled to main portion 100a in situ as is as is known in the art.

Stent-graft portion 100a comprises a bifurcated tubular member 101 comprising any suitable graft material and annular undulating wire spring elements or stents 102, which structurally support bifurcated tubular graft 101 as is conventional in the art. Tubular graft 101 can be positioned on the interior and/or exterior of wire spring elements 102. The prosthesis also includes undulating wire support spring 104 at the proximal end thereof to provide radial strength. Spring 102 also can be positioned on the interior and/or exterior tubular graft 101. Another such wire support spring (not shown) can be provided along the distal end portion of the ipsilateral leg portion of tubular graft 101.

Contralateral leg portion 100b comprises a tubular graft member and annular wire springs or stents 102, which can be secured to the graft member in the same manner as springs 102 are coupled to bifurcated tubular graft member 301. Further, graft material can extend into the apices of the proximal spring 110 of the contralateral leg as shown in FIG. 9. Proximal spring 110 can be biased radially outward to enhance the connection to the contralateral portion of bifurcated tubular member 101 when inserted therein.

The spring elements and support springs can be of any suitable material as would be apparent to one of ordinary skill in the art. One suitable material is nitinol. The graft material for any of the prostheses described herein also can be any suitable material such as Dacron® or expanded polytetrafluoroethylene (ePTFE).

Radiopaque markers 106 and 108 as is known in the art also can be provided to facilitate positioning the stent-graft portions at the desired location using traditional fluoroscopic techniques. Such markers are secured to the prosthesis as known in the art.

Any feature described in any one embodiment described herein can be combined with any other feature of any of the other embodiments.

Variations and modifications of the devices and methods disclosed herein will be readily apparent to persons skilled in the art.

What is claimed is:

1. A method of securing a stent-graft prosthesis placed at a desired site in a passageway of a human body using a support member having first and second fasteners releasably coupled thereto comprising:
   delivering a support member having releasably coupled thereto first and second fasteners, each having a proximal piercing end portion and a distal piercing end portion, to a site where a stent-graft prosthesis, which has a tubular wall, has been placed in the passageway, which has a wall;
   advancing the proximal piercing end portion of a first one of the first and second fasteners beyond the prosthesis;
   penetrating the proximal piercing end portion of said first one of the fasteners into the wall of the fasteners through the tubular wall of the prosthesis;
   passing the distal piercing end portion of said first one of the fastneners through the tubular wall of the prosthesis and into the wall of the passageway;
   deploying a second one of the first and second fasteners and attaching it to the passageway wall such that its proximal piercing end portion is penetrated into the wall of the passageway without passing through the tubular wall of the prosthesis and its distal piercing end portion is passed through the tubular wall of the prosthesis and into the wall of the passageway;
   wherein the piercing end portions of said first one of the fasteners are penetrated into the wall sequentially and the piercing end portions of said second one of the fasteners are penetrated into the wall sequentially; and
   withdrawing the support member and leaving the fasteners, which fix the prosthesis to the passageway wall, in the passageway wall.

2. The method of claim 1 wherein the fasteners are releasably secured to the support member such that the fasteners are delivered with the proximal piercing end portions leading the distal piercing portions.

3. The method of claim 1 wherein a radially expandable member is positioned in the passageway and expanded to force the piercing end portions of said first one of the fasteners into the wall of the passageway such that they penetrate the wall of the passageway.

4. The method of claim 3 wherein the radially expandable member is a balloon which is positioned in the passageway and inflated to force the piercing end portions of said first one of the fasteners into the wall of the passageway.

5. The method of claim 3 wherein the radially expandable member has releasably secured thereto said first one of said fasteners and is one of two sheathed self-expanding members that form arms of said support member and are positioned in the passageway and are unsheathed to radially expand and force the piercing end portions of said first one of the fasteners into the wall of the passageway.

6. The method of claim 5 wherein at least one of said arms has a channel having an opening that is narrowed along a section of the channel and that releasably retains a portion of said first one of said fasteners along said section, which retained fastener portion has a width greater than the width of the narrowed opening, and said second one of said fasteners is releasably retained in another section of said channel, and fasteners are sequentially deployed.

7. The method of claim 1 wherein the first and second fasteners are deppployed simultaneously.

8. The method of claim 1 wherein said support member is disposed in a sheath and comprises first and second members each having a preshaped curved memory configuration and both being positioned in the passageway in a restrained second configuration in said sheath and allowed to move toward the preshaped memory configuration when unsheathed to force the piercing portions of said first one of the fasteners and thereafter the piercing portions of the second one of the fasteners, which fasteners are releasable secured to one of said preshaped members, into the wall of the passageway.

9. The method of claim 1 wherein said first one of the fasteners has V-shaped portions, each forming one of said piercing end portions of said first one of the fastener, which piercing portions each further include a barb.

10. The method of claim 1 wherein the fasteners are endoluminally delivered through a vessel.

11. The method of claim 10 wherein the first one of the fasteners is positioned in a first vessel with its proximal piercing end portion upstream of a second vessel that branches from the first vessel and its distal piercing end portion downstream of the second vessel.

12. The method of claim 11 wherein the fasteners are positioned in the aorta of the patient with the proximal piercing end portions upstream of a renal artery and the distal piercing end portions downstream of said renal artery.

13. The method of claim 1 wherein each fastener has two V-shaped portions coupled to one another through a flexible member, each V-shaped portion forming a piercing end portion and said piercing end portions extend generally radially outward from said support, which together with said fasteners are slidably disposed in a sheath.

14. The method of claim 1 wherein each fastener has a central portion, which is disposed between the proximal and distal piercing end portions of the fastener and which comprises a thread.

15. The method of of claim 1 wherein each fastener has a central portion, which is disposed between the proximal and distal piercing end portions of the fastener and which comprises a suture.

16. The method of claim 1 wherein each fastener has a central portion, which is disposed between the proximal and distal piercing end portions of the fastener and which comprises a wire.

17. The method of claim 1 wherein the support member is in a tubular member and moved relative thereto to expose the proximal piercing end portion of said first one of the fasteners.

18. The method of claim 17 wherein the support member includes an expandable member which is expanded to push the exposed proximal piercing end portion of said first one of said fasteners into the passageway wall.

19. The method of claim 18 wherein after the proximal piercing end portion of said first one of said fasteners has been pushed into the passageway way, the support member and tubular member are moved relative to one another to expose the distal piercing end portion of that fastener.

20. The method of claim 19 wherein the expandable member is expanded to push the distal piercing end portion of said first one of the fasteners through the prosthesis wall and into the passageway wall.

21. The method of claim 1 wherein the fastener support member is delivered in a tubular member with a plurality of expandable balloons positioned between each fastener and the tubular member and secured to the fastener support member.

22. The method of claim 21 wherein each balloon is aligned with one off the fasteners.

23. The method of claim 22 wherein the fasteners are axially aligned along the fastener support member.

24. The method of claim 1 wherein the support member comprises two self-expanding arms disposed in a sheath and adapted to expand radially when unsheathed, each arm having one of said first and second fasteners releasably secured thereto.

25. The method of claim 24 wherein each arm has channel having an opening that is narrowed along a section of the channel and that releasably locks a portion of one of said fasteners along said section, which fastener portion has a width greater than the width of the narrowed opening.

26. The method of claim 1 wherein the fasteners are delivered in a tubular sheath, the proximal piercing end portion of the first fastener is extended from the tubular sheath before penetrating it into the wall of the first passageway, and the distal piercing end portion of the first one of said fasteners is extended from the tubular sheath before passing it through the wall of the prosthesis and into the wall of the passageway.

27. The method of claim 1 wherein said second one of the fasteners is deployed such that it is circumferentially spaced from said first one of the fasteners.

28. A method of securing a stent-graft prosthesis placed at a desired site in a passageway of a human body using a support member having fasteners releasably coupled thereto comprising:
    delivering a support member having releasably coupled thereto a plurality of fasteners, each having a proximal piercing end portion and a distal piercing end portion, to a site where a stent-graft prosthesis, which has a tubular wall, has been placed in the passageway, which has a wall;
    advancing the proximal piercing end portion of a first one of the fasteners beyond the prosthesis;
    penetrating the proximal piercing end portion of said first one of the fasteners into the wall of the passageway without passing the proximal piercing end portion of said first one of the fasteners through the tubular wall of the prosthesis;
    passing the distal piercing end portion of said first one of the fasteners through the tubular wall of the prosthesis and into the wall of the passageway;
    deploying a second one of the fasteners and attaching it to the passageway wall such that its proximal piercing end portion is penetrated into the wall of the passageway without passing through the tubular wall of the prosthesis and its distal piercing end portion is passed through the tubular wall of the prosthesis and into the wall of the passageway;
    withdrawing the support member and leaving the fasteners, which fix the prosthesis to the passageway wall, in the passageway wall;
    wherein the distal piercing end position of said first one of the fasteners is pushed through the prosthesis wall and into the passageway wall after the proximal piercing end portion of that fastener is penetrated into the wall of the passageway.

29. A method of securing a prosthesis placed as a desired site in a passageway of a human body comprising:
    after a prosthesis having a tubular wall has been deployed in a first passageway in a human body adjacent to one side of a branch passageway that branches from the first passageway, which has a wall, endovascularly delivering first and second fasteners, each having a proximal piercing end portion and a distal piercing end portion and being releasably secured to support member, through the first passageway such that the proximal piercing end portion of the first fastener is beyond the prosthesis at a location on the other side of the branch passageway;
    penetrating the proximal piercing end portion of the first fastener into the wall of the first passageway at a location beyond the prosthesis and on the other side of the branch passageway as compared to the prosthesis without passing into proximal piercing end portion of the first fastener through the tubular wall of the prosthesis; and
    after the proximal piercing end portion of the first fastener is penetrated into the wall of the first passageway pushing the distal piercing end portion of the first fastener through the prosthesis wall and penetrating it into the first passageway wall;
    rotating the support member to deploy the second fastener at a location that is circumferentially spaced from said first fastener and penetrating the proximal piercing end portion of the second fastener into the wall of the first passageway without passing the proximal piercing end portion of the second fastener through the tubular wall of the prosthesis and thereafter pushing the distal piercing end portion of the second fastener through the prosthesis wall and into the first passageway wall such that it penetrates the first passage passageway wall with the second fastener being circumferentially spaced from the first fastener.

30. The method of claim 29 wherein the support member is in a tubular member and the support member and tubular member are moved relative to one another to expose the proximal piercing end portions of the fasteners, which are axially spaced from one another, prior to penetrating the proximal piercing end portions into the wall of the first passageway.

31. The method of claim 30 wherein the support member includes and expandable member which is expanded to push the exposed first piercing end portion of the first fastener into the first passageway wall.

32. The method of claim 31 wherein after the proximal piercing end portion of the fastener has been pushed into the first passageway wall, the support member and tubular member are moved relative to one another to expose the distal piercing end portion of the first fastener.

33. The method of claim 31 wherein the expandable member is a balloon.

34. The method of claim 32 wherein the expandable member is expanded to push the distal piercing end portion of the first fastener through the prosthesis wall and into the first passageway wall.

35. the method of claim 29 wherein a plurality of balloons are used to force the piercing end portions into the wall of the first passageway.

36. The method of claim 29 wherein the prosthesis is a stent-graft prosthesis.

37. The method of claim 29 wherein the fasteners are axially aligned when releasably secured to the support member.

38. The method of claim 37 wherein the fastener support member is delivered in a tubular member with a plurality of expandable balloons positioned between each fastener and the tubular member and secured to the fastener support member.

39. The method of claim 38 wherein each balloon is aligned with one of the fasteners.

* * * * *

UNITED STATES PATENT AND TRADEMARK OFFICE
CERTIFICATE OF CORRECTION

| | | |
|---|---|---|
| PATENT NO. | : 7,955,380 B2 | Page 1 of 1 |
| APPLICATION NO. | : 11/276877 | |
| DATED | : June 7, 2011 | |
| INVENTOR(S) | : Jack Chu et al. | |

It is certified that error appears in the above-identified patent and that said Letters Patent is hereby corrected as shown below:

IN THE CLAIMS:

Column 13, line 63, claim 7, "are depployed" should be changed to --are deployed--

Column 14, line 50, claim 19, "into the passageway way" should be changed to --into the passageway--

Column 14, line 63, claim 22, "one off the" should be changed to --one of the--

Column 15, line 4, claim 25, "are has channel" should be changed to --arm has a channel--

Column 15, line 55, claim 29, "places as a desired" should be changed to --places at a desired--

Column 15, line 63, claim 29, "secured to support" should be changed to --secured to a support--

Column 16, line 23, claim 29, "first passage passageway" should be changed to --first passageway--

Signed and Sealed this
Sixth Day of December, 2011

David J. Kappos
*Director of the United States Patent and Trademark Office*